US008656934B2

(12) United States Patent
Forgione

(10) Patent No.: US 8,656,934 B2
(45) Date of Patent: Feb. 25, 2014

(54) HAIR TREATMENT DEVICE

(76) Inventor: Barbara Forgione, Tampa, FL (US)

(*) Notice: Subject to any disclaimer, the term of this patent is extended or adjusted under 35 U.S.C. 154(b) by 114 days.

(21) Appl. No.: 12/927,643

(22) Filed: Nov. 19, 2010

(65) Prior Publication Data

US 2012/0125357 A1 May 24, 2012

(51) Int. Cl.
A45D 24/00 (2006.01)
A45D 7/04 (2006.01)
A45D 19/18 (2006.01)
A45D 2/00 (2006.01)

(52) U.S. Cl.
USPC ........... 132/207; 132/200; 132/203; 132/222; 132/270

(58) Field of Classification Search
USPC ......... 132/270, 200, 202, 203, 207, 208, 209, 132/210, 212, 163, 221, 222, 223, 241, 243, 132/274, 273, 319, 320, 245, 246, 108, 109, 132/112; 401/9, 10, 207, 196, 203, 261; D28/7, 39, 41
See application file for complete search history.

(56) References Cited

U.S. PATENT DOCUMENTS

| | | | |
|---|---|---|---|
| 2,655,924 A * | 10/1953 | Petitta | 132/212 |
| 3,101,724 A * | 8/1963 | Nizetich | 132/270 |
| 3,128,778 A * | 4/1964 | Ricci et al. | 132/212 |
| 3,295,535 A * | 1/1967 | Amato | 132/212 |
| 3,640,288 A * | 2/1972 | Spanel | 132/212 |
| 3,662,767 A * | 5/1972 | Murtha | 132/212 |
| 3,800,811 A * | 4/1974 | Esposto | 132/270 |
| 3,805,810 A * | 4/1974 | Savala | 132/270 |
| 3,968,805 A * | 7/1976 | Sobeck, Jr. | 132/270 |
| 4,144,897 A * | 3/1979 | Mosz | 132/270 |
| 5,042,514 A * | 8/1991 | Bastien | 132/270 |
| 5,056,538 A * | 10/1991 | Matula | 132/208 |
| 5,228,465 A * | 7/1993 | Hill | 132/212 |
| 5,771,906 A * | 6/1998 | De Benedictis | 132/207 |
| 6,035,862 A * | 3/2000 | Di Luca | 132/270 |
| 6,626,599 B2 * | 9/2003 | De Laforcade | 401/10 |
| 6,647,989 B1 * | 11/2003 | De Benedictis | 132/210 |
| 6,746,165 B2 * | 6/2004 | de Laforcade | 401/10 |
| 7,000,619 B2 * | 2/2006 | Winckels et al. | 132/208 |
| 7,305,995 B2 * | 12/2007 | Tojo et al. | 132/222 |
| 7,425,220 B2 * | 9/2008 | Barrass et al. | 8/405 |
| 7,500,487 B2 * | 3/2009 | Kobayashi et al. | 132/222 |
| 2003/0000541 A1 * | 1/2003 | Smith | 132/210 |
| 2006/0157078 A1 * | 7/2006 | Tojo et al. | 132/222 |
| 2007/0068547 A1 * | 3/2007 | Gurth et al. | 132/200 |
| 2008/0223391 A1 * | 9/2008 | Baker et al. | 132/202 |

FOREIGN PATENT DOCUMENTS

GB 2234758 A * 2/1991 ............. A45D 19/02

* cited by examiner

Primary Examiner — Vanitha Elgart
(74) Attorney, Agent, or Firm — Arthur W. Fisher, III

(57) ABSTRACT

A hair treatment device or tool to chemically treat a section of hair for highlighting, frosting, perming, coloring, decoloring, straightening, neutralizing, relaxing, conditioning and the like comprising a member or body of lightweight, flexible, resilient, washable, porous, absorbent foam or fabric including at least one hair section treatment channel formed therein extending from the surface thereof to receive a section of hair therein coated or covered with a treating chemical to isolate the section of hair during treatment and absorb excess chemical from the section of hair being treated.

3 Claims, 6 Drawing Sheets

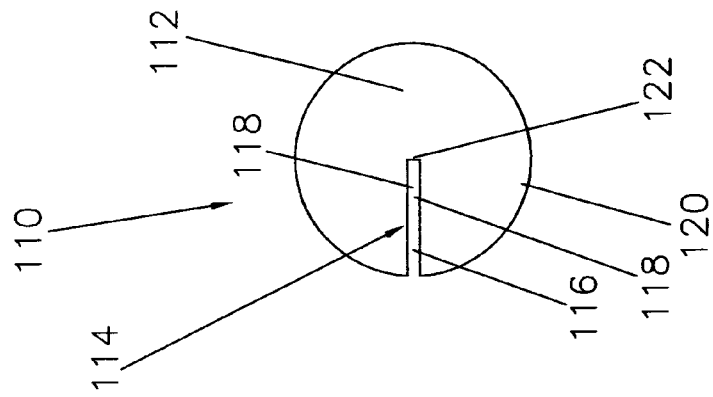
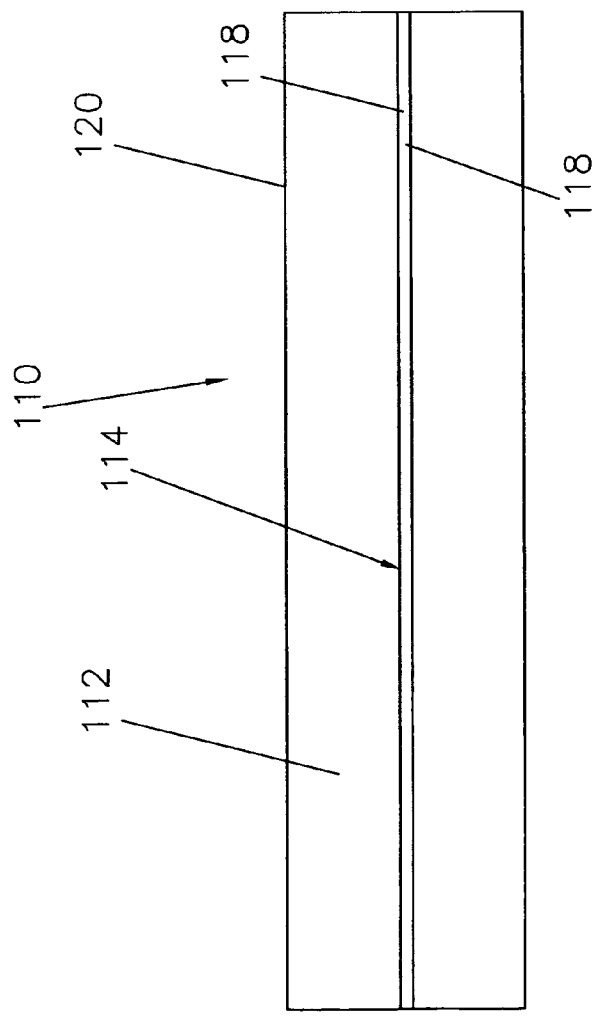
FIG. 4
FIG. 3

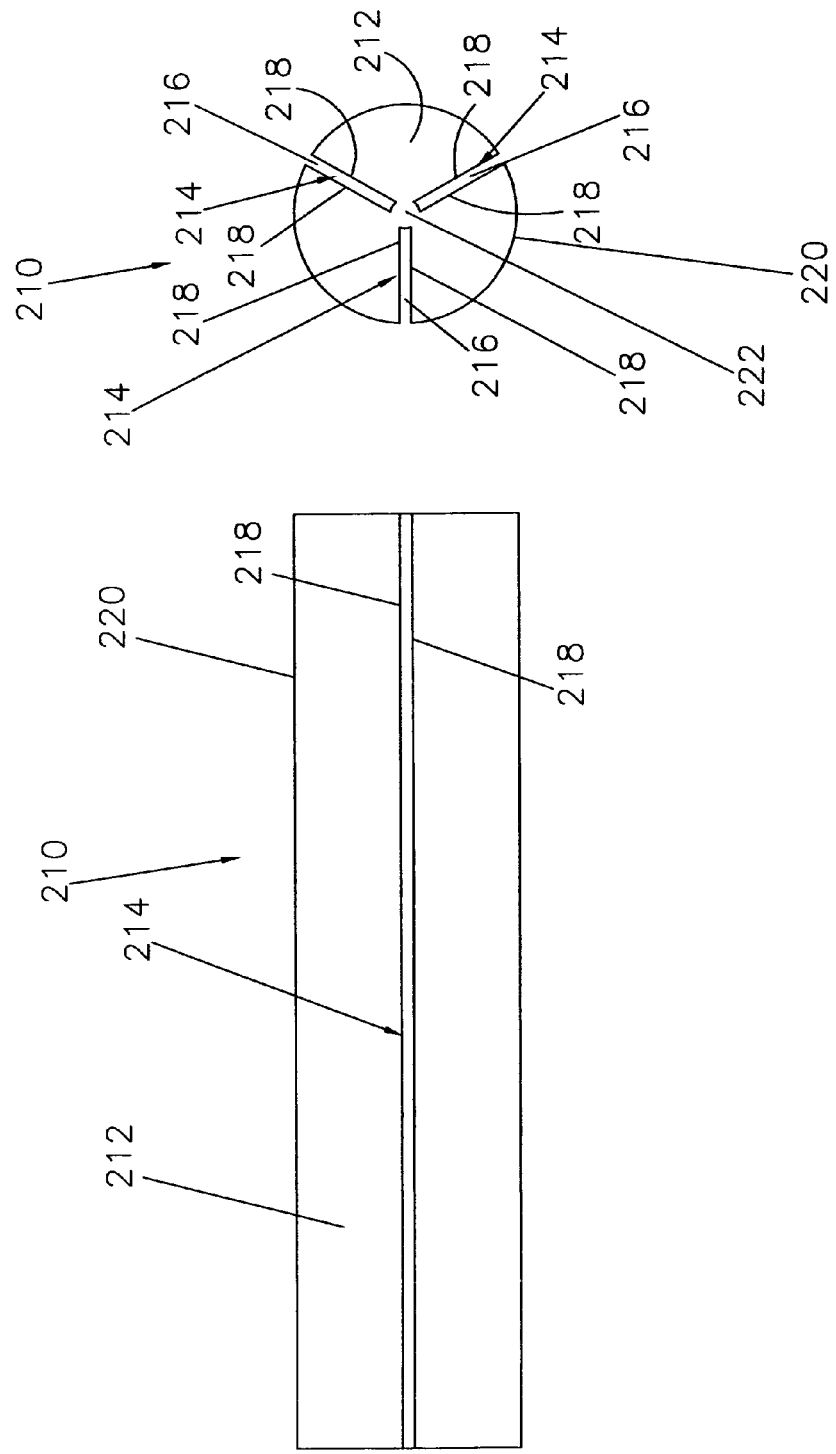

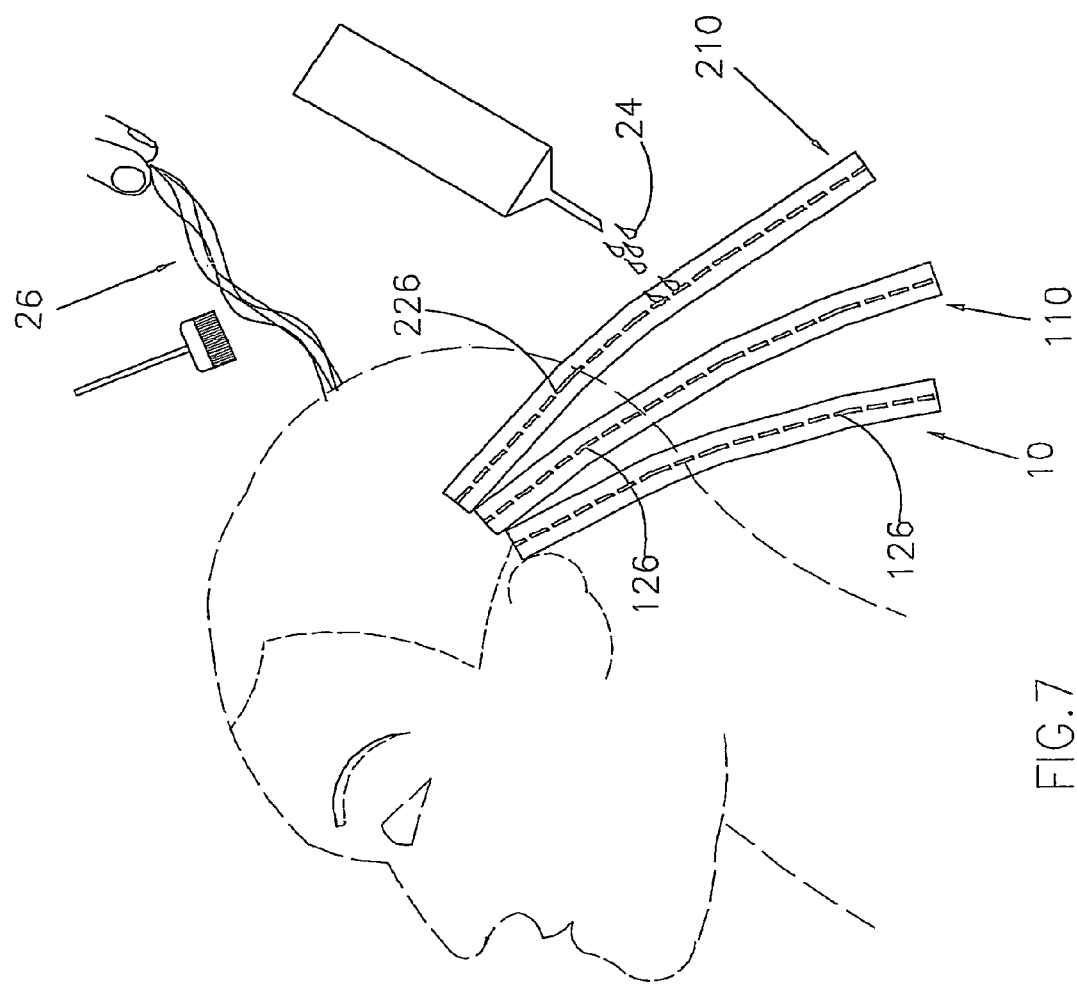

HAIR TREATMENT DEVICE

BACKGROUND OF THE INVENTION

1. Field of the Invention

A hair treatment device or tool to chemically treat a section of hair.

2. Description of the Prior Art

Numerous devices have been developed to chemically treat hair for highlighting, frosting, perming, coloring, decoloring, straightening, neutralizing, relaxing, conditioning and the like.

U.S. Pat. No. 3,662,767 shows a clamp to hold a woman's hair in small bunches to permit selective dyeing at the roots. The clamp comprises a plastic shell with resilient plastic opposed members for frictionally clamping a small bunch of hair and holding the hair away from the head.

U.S. Pat. No. 3,941,613 relates to a hair frosting device comprising a container hinged on one side and snapped latched on the other so that it can be opened for placing a strand of hair therein. An opening at one end thereof is notched on one part of the container with cooperating notches on the other part for pulling the hair strand through and positioning it after which the container is filled with a hair treating liquid and closed. This allows the isolated treatment of one or more strands of hair without the problem of treating adjacent strands which are not desired to be treated.

U.S. Pat. No. 4,503,870 shows a coiffure styling device comprising a pair of elongated body members hinged along adjacent edges for closing the device around strands of hair. Attached along the free edges of the body members by stems are complementary hemispherical nodules with rounded camming surfaces and flat engaging surfaces which snap-lock together when the body member halves are hinged to a closed portion. At one or both ends of each body member half is formed a flange flared outwardly to form a base of expanded surface area to support the styling device diametrically outwardly from the scalp of a person. On the inner faces of each body member is a groove for accommodating the hair strands and for containing adequate styling fluids.

U.S. Pat. No. 6,746,165 and U.S. Pat. No. 6,626,599 teach an applicator device for applying product to at least one section of hair includes an elastically deformable component, a reservoir for the product, and a slot at least partially defined by the elastically deformable component. The slot is bounded by edges and is configured to receive a section of hair between the edges. The slot comprises a first slot portion lying in a first plane and at least one second slot portion lying in a second plane different from the first plane.

EP 1,481,605 relates to rolling a lock of hair around a support forming a curl around it. One end of the lock is held in a resiliently deformed slot in the support. The capillary product is applied onto the lock, coating at least part which is rolled around the outer periphery of the support.

Additional examples of the prior art are found in U.S. Pat. No. 3,128,778; U.S. Pat. No. 3,198,196; U.S. Pat. No. 3,452,759; U.S. Pat. No. 3,805,810; U.S. Pat. No. 4,385,638 and U.S. Pat. No. 5,588,449.

SUMMARY OF THE INVENTION

The present invention relates to a hair treatment device or tool to chemically treat a section of hair for highlighting, frosting, perming, coloring, decoloring, straightening, neutralizing, relaxing, conditioning and the like.

The hair treatment device or tool comprises a body constructed of a lightweight, flexible, resilient, absorbent material having at least one hair section treatment channel extending substantially the length thereof.

Chemical is applied directly to each section of hair to be treated before each section of hair is placed or positioned in a hair section treatment channel.

Alternately, chemical may be placed into the hair section treatment channels before sections of hair are placed in the hair section treatment channels.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 3 is a top view of the hair treatment device or tool of the present invention including an alternate embodiment of a hair section treatment channel.

FIG. 4 is an end view of the hair treatment device or tool of the present invention including an alternate embodiment of a hair section treatment channel of FIG. 3.

FIG. 5 is a top view of the hair treatment device or tool of the present invention including another alternate embodiment of a hair section treatment channel.

FIG. 6 is an end view of the hair treatment device or tool of the present invention including an alternate embodiment of a hair section treatment channel of FIG. 5.

FIG. 7 depicts the application of chemical to a section of hair using the hair treatment device or tool of the present invention.

Similar reference characters refer to similar parts throughout the several views of the drawings.

DETAILED DESCRIPTION OF THE PREFERRED EMBODIMENT

Figure 2:
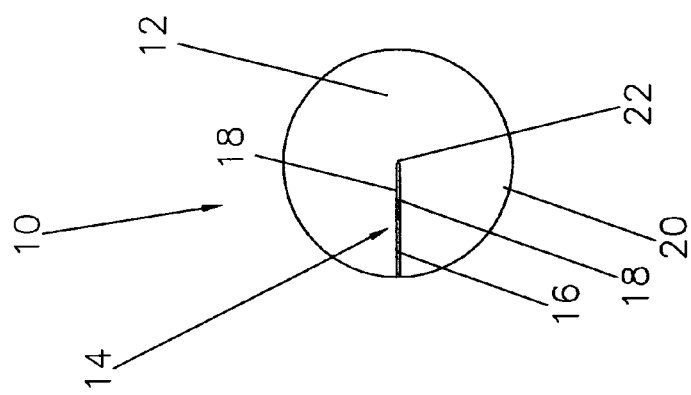
FIG. 2 is an end view of the hair treatment device or tool of the present invention including a hair section treatment channel of FIG. 1.
Figure 1:
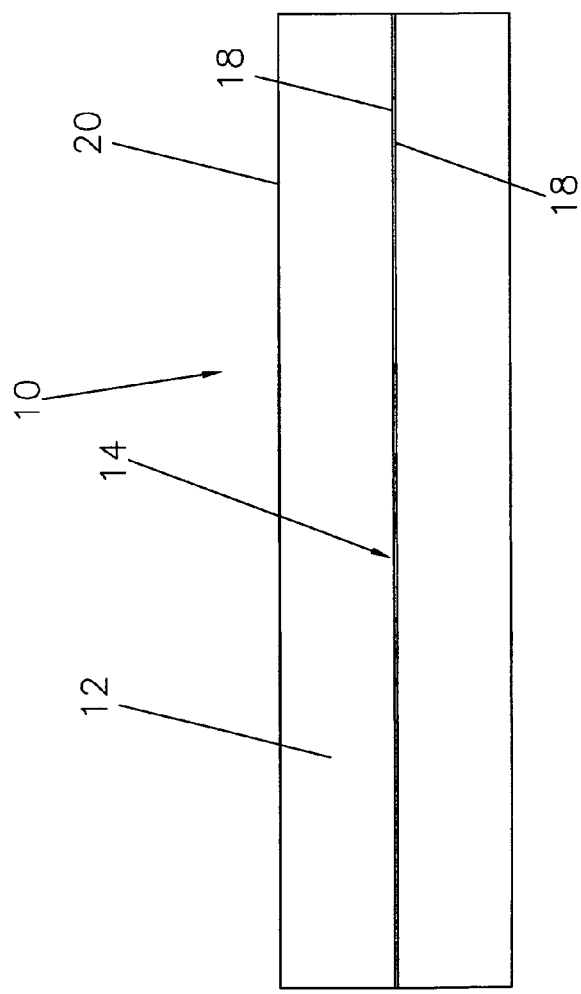
FIG. 1 is a top view of the hair treatment device or tool of the present invention including a hair section treatment channel.

As shown in FIGS. 1 and 2, the present invention relates to a hair treatment device or tool generally indicated as 10 to chemically treat a section of hair for highlighting, frosting, perming, coloring, decoloring, straightening, neutralizing, relaxing, conditioning and the like.

The hair treatment device or tool 10 comprises a substantially cylindrical body 12 having a hair section treatment channel 14 extending substantially the length thereof. Of course, the hair section treatment channel 14 may extend the entire length of the substantially cylindrical body 12.

The substantially cylindrical body 12 is constructed of a lightweight, flexible, resilient, washable, porous, absorbent foam or fabric.

As best shown in FIG. 2, the hair section receiving channel 14 comprises a slit 16 including two absorbent interior surfaces 18 extending from the outer surface 20 of the substantially cylindrical body 12 to substantially the center 22 thereof.

FIGS. 3 and 4 show an alternate embodiment of the hair treatment device or tool generally indicated as 110. Specifically, the hair treatment device or tool 110 comprises a substantially cylindrical body 112 having a hair section treatment channel 114 extending substantially the length thereof. Of course, the hair section treatment channel 114 may extend the entire length of the substantially cylindrical body 112.

The substantially cylindrical body 112 is constructed of a lightweight, flexible, resilient, washable, porous, absorbent foam or fabric.

As best shown in FIG. 4, the hair section receiving channel 114 comprises a slot or groove 116 including two absorbent interior surfaces 118 extending from the outer surface 120 of the substantially cylindrical body 112 to substantially the center 122 thereof and a third absorbent interior surface 118.

FIGS. 5 and 6 show another alternate embodiment of the hair treatment the hair treatment device or tool generally indicated as 210. Specifically, the hair treatment device or tool 210 comprises a substantially cylindrical body 212 having a plurality of hair section treatment channels 214 extending substantially the length thereof. Of course, the hair section treatment channel 214 may extend the entire length of the substantially cylindrical body 212.

The substantially cylindrical body 212 is constructed of a lightweight, flexible, resilient, washable, porous, absorbent foam or fabric.

As best shown in FIG. 6, each hair section receiving channel 214 comprises a slot or groove 216 including two absorbent interior surfaces 218 extending from the outer surface 220 of the substantially cylindrical body 212 to substantially the center 222 thereof and a third absorbent interior surface 218.

The method of using the hair treatment device or tool 10/110/210 is depicted in FIG. 7. Specifically, chemical 24 may be dispensed from a bottle and applied directly to each section of hair 26/126/226 to be treated before each section of hair 26/126/226 is placed or positioned in a hair section treatment channel 14/114/214.

Of course, chemical 24 may be applied with a brush or digitally by the thumb and index finger.

Alternately, chemical 24 may be placed into the hair section treatment channels 14/114/214 before the sections of hair 26/126/226 are placed in the hair section treatment channels 14/114/214.

Otherwise, each section of hair 26/126/226 may be placed or positioned in a hair treatment channel 14/114/214 before chemical 24 is applied to each section of hair 26/126/226.

In application, the chemical may be evenly spread over the sections of hair 26/126/226 by digitally massaging or squeezing the substantially cylindrical body 12/112/212. In addition, the porosity of the interior surfaces 18/118/218 of the substantially cylindrical bodies 12/112/212 allow excess chemical to be absorbed into the interior surfaces 22/122/222 of the hair section treatment channels 14/114/214.

Once the chemical has had sufficient time to effectively react with the hair sections 26/126/226, the hair treatment devices or tools 10/110/210 are removed and washed for reuse.

Since the sections of hair 26/126/226 are isolated in the corresponding hair section treatment channel 14/114/214, the chemical 24 does not dry or affect hair not intended to be treated.

Figure 9:
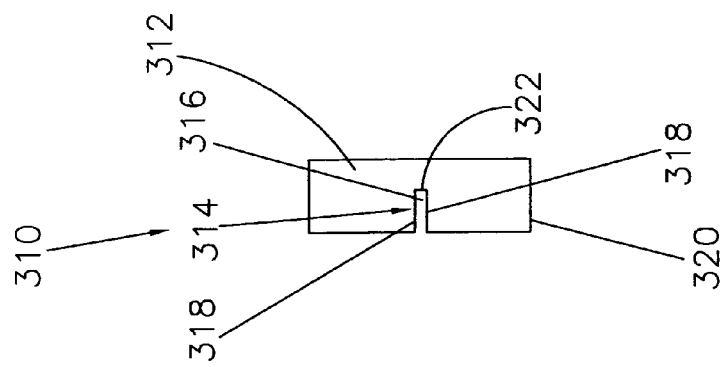
FIG. 9 is an end view of the hair treatment device or tool of the present invention including an alternate embodiment of a hair section treatment channel of FIG. 8.
Figure 8:
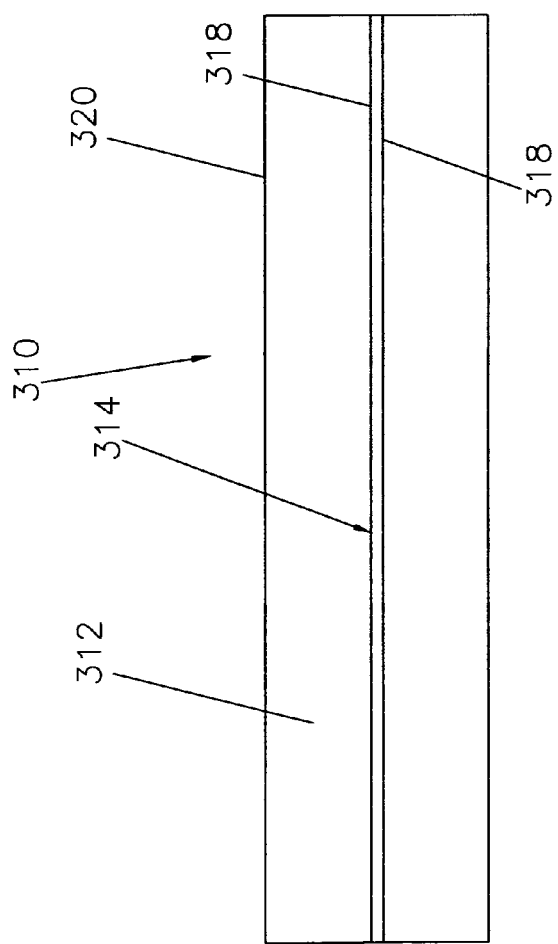
FIG. 8 is a top view of the hair treatment device or tool of the present invention including yet another embodiment of a hair treatment device or tool of the present invention including a hair section treatment channel.

FIGS. 8 and 9 show yet another alternate embodiment of the hair treatment device or tool generally indicated as 310. Specifically, the hair treatment device or tool 310 comprises a substantially rectilinear body 312 having a hair section treatment channel 314 extending substantially the length thereof. Of course, the hair section treatment channel 314 may extend the entire length of the substantially rectilinear body 312.

The substantially rectilinear body 312 is constructed of a lightweight, flexible, resilient, washable, porous, absorbent foam or fabric.

As best shown in FIG. 9, the hair section receiving channel 314 comprises a slot or groove 316 including two absorbent interior surfaces 318 extending from the outer surface 320 of the substantially rectilinear body 312 to the center 322 thereof and a third absorbent interior surface 318.

Figures 10, 11:
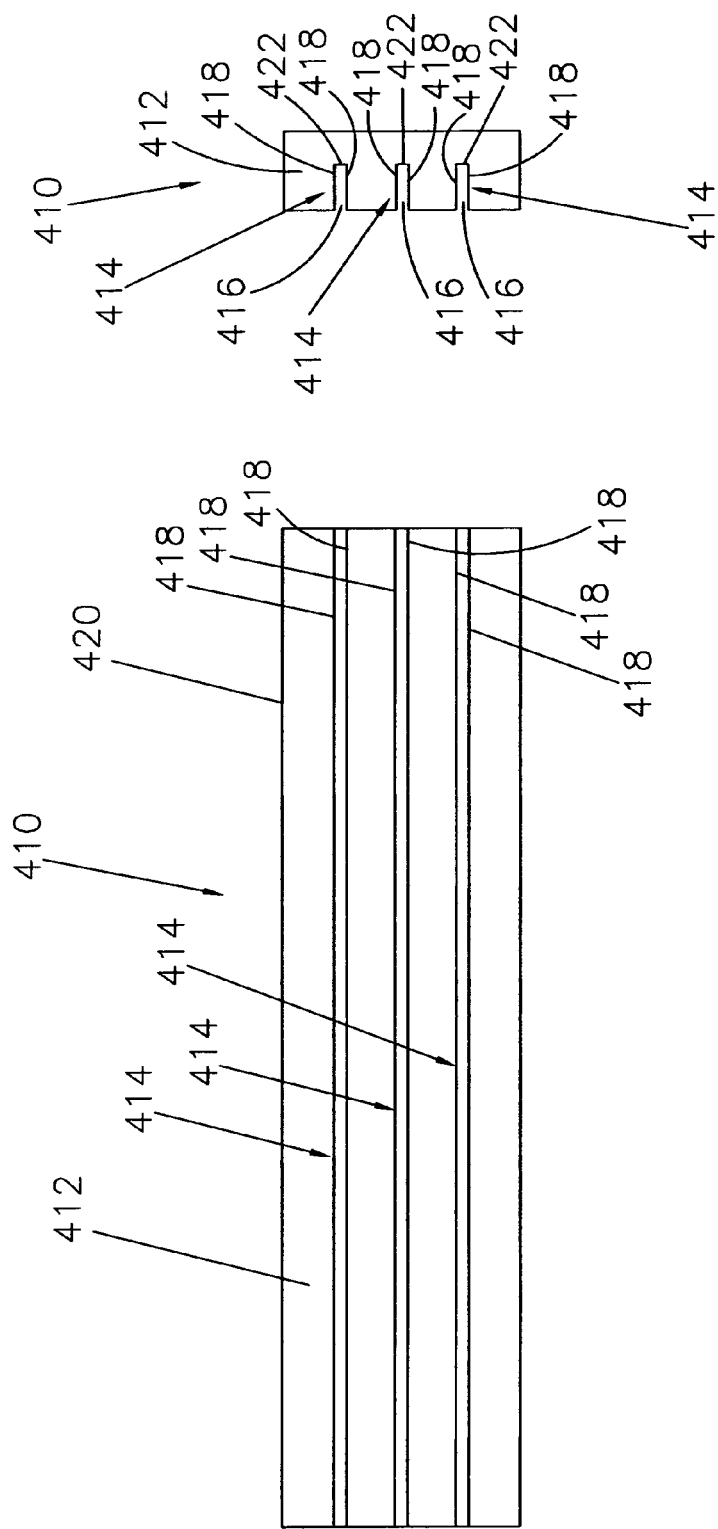
FIG. 10 is a top view of the hair treatment device or tool of the present invention including still yet another alternate embodiment of a hair treatment device or tool of the present invention including hair section treatment channel.
FIG. 11 is an end view of the hair treatment device or tool of the present invention including an alternate embodiment of a hair section treatment channel of FIG. 10.

FIGS. 10 and 11 show yet still another alternate embodiment of the hair treatment device or tool generally indicated as 410. Specifically, the hair treatment device or tool 410 comprises a substantially rectilinear body 412 having a plurality of hair section treatment channels 414 extending substantially the length thereof. Of course, the hair section treatment channel 414 may extend the entire length of the substantially rectilinear body 412.

The substantially rectilinear body 412 is constructed of a lightweight, flexible, resilient, washable, porous, absorbent foam or fabric.

As best shown in FIG. 11, each hair section receiving channel 414 comprises a slot or groove 416 including two absorbent interior surfaces 418 extending from the outer surface 420 of the substantially rectilinear body 412 to substantially the center 422 thereof and a third absorbent interior surface 418.

Although substantially cylindrical or substantially rectilinear bodies 12, 112, 212, 312 and 412 of foam are depicted, foam sheets may be used to wrap the sections of hair.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A hair treatment applicator to chemically treat a section of hair for highlighting, frosting, perming, coloring, decoloring, straightening, neutralizing, relaxing, or conditioning comprising an elongated body of flexible, resilient porous material having an outer surface and an inner core including at least one hair section treatment channel extending from said outer surface into said inner core of said elongated body, said hair section treatment channel including at least two interior absorbent surfaces, said channel retaining the entire length of a section of hair to be treated and separating the section of hair to be treated from adjacent strands of hair while said elongated body of flexible resilient porous material and the section of hair are manually manipulated to distribute a treating chemical over the section of hair within said hair section treatment channel and to shield the section of hair to be treated from the environs to reduce the effects of temperature and humidity on the treating chemical.

2. A method of chemically treating a section of hair for highlighting, frosting, perming, coloring, decoloring, straightening, neutralizing, relaxing, or conditioning comprising an elongated body of flexible, resilient porous material having an outer surface and an inner core including at least one hair section treatment channel extending from said outer surface into said inner core of said elongated body, said hair section treatment channel including at least two interior absorbent surfaces, said channel retaining the entire length of a section of hair to be treated with a treating chemical and separating the section of hair to be treated from adjacent strands of hair while allowing said elongated body of flexible resilient porous material and section of hair to be manually manipulated to distribute the treating chemical over the section of hair within said hair section treatment channel and to shield the section of hair to be treated from the environs to reduce the effects of temperature and humidity on the treating chemical, said method comprising the steps of:

forming a section of hair applying the treating chemical to the section of hair placing the section of hair in the hair section treatment channel manipulating the flexible, resilient, porous material to distribute the treating chemical over and through the section of hair squeezing the flexible, resilient, porous material to allow excess treatment chemical to be absorbed into the interior absorbent surfaces allowing the treating chemical to effectively treat the section of hair and removing the section of hair from the elongated body.

3. A method of chemically treating a section of hair for highlighting, frosting, perming, coloring, decoloring, straightening, neutralizing, relaxing, or conditioning comprising an elongated body of flexible, resilient porous material having an outer surface and an inner core including at least one hair section treatment channel extending from said outer surface into said inner core of said elongated body, said hair section treatment channel including at least two interior absorbent surfaces, said channel retaining the entire length of a section of hair to be treated with a treating chemical and separating the section of hair to be treated from adjacent strands of hair while allowing said elongated body of flexible resilient porous material and section of hair to be manually manipulated to distribute the treating chemical over the section of hair within said hair section treatment channel and to shield the section of hair to be treated from the environs to reduce the effects of temperature and humidity on the treating chemical, said method comprising the steps of:

forming a section of hair placing the section of hair in the hair section treatment channel applying the treating chemical to the section of hair manipulating the flexible, resilient, porous material to distribute the treating chemical over and through the section of hair squeezing the flexible, resilient, porous material to allow excess treatment chemical to be absorbed into the said interior absorbent surfaces allowing the treating chemical to effectively treat the section of hair and removing the section of hair from the hair elongated body.

\* \* \* \* \*